United States Patent
Harro et al.

(10) Patent No.: US 11,182,721 B2
(45) Date of Patent: Nov. 23, 2021

(54) HEALTHCARE RISK ANALYTICS

(71) Applicant: International Business Machines Corporation, Armonk, NY (US)

(72) Inventors: Cindy Harro, New Fairfield, CT (US); Mark E. Elliott, Cary, NC (US); Thomas H. Rogers, Raleigh, NC (US); Paul R. Bastide, Boxford, MA (US); Aashita Shekhar, Shrewsbury, MA (US); Rohit Ranchal, Middlesex, MA (US)

(73) Assignee: International Business Machines Corporation, Armonk, NY (US)

( * ) Notice: Subject to any disclaimer, the term of this patent is extended or adjusted under 35 U.S.C. 154(b) by 658 days.

(21) Appl. No.: 15/986,091

(22) Filed: May 22, 2018

(65) Prior Publication Data

US 2019/0362277 A1    Nov. 28, 2019

(51) Int. Cl.
G06Q 10/06     (2012.01)
G06N 3/08      (2006.01)
G06Q 50/00     (2012.01)
G06Q 50/22     (2018.01)

(52) U.S. Cl.
CPC ......... *G06Q 10/0635* (2013.01); *G06N 3/084* (2013.01); *G06Q 50/01* (2013.01); *G06Q 50/22* (2013.01)

(58) Field of Classification Search
CPC .... G06Q 10/0635; G06Q 50/01; G06Q 50/22; G06N 3/084
USPC ....................................................... 705/7.28
See application file for complete search history.

(56) References Cited

U.S. PATENT DOCUMENTS

| | | | |
|---|---|---|---|
| 8,201,256 B2 | 6/2012 | Patanella | |
| 8,762,178 B2 | 6/2014 | Ruggieri et al. | |
| 9,699,209 B2 | 7/2017 | Ng et al. | |
| 2003/0004754 A1 | 1/2003 | Krutz | |
| 2005/0071185 A1* | 3/2005 | Thompson | G06Q 10/10 705/317 |
| 2006/0059073 A1* | 3/2006 | Walzak | G06Q 40/025 705/35 |

(Continued)

OTHER PUBLICATIONS

Riskwatch Upgrades HIPAA Security Risk Analysis Software. Productivity Software 17.7: N/A. Worldwide Videotex. (Jul. 1, 2004).*

(Continued)

*Primary Examiner* — Timothy Padot
(74) *Attorney, Agent, or Firm* — VanLeeuwen & VanLeeuwen; William J. Stock

(57) ABSTRACT

An approach is provided in which an information handling system trains on a set of historical data that includes a set of first infractions caused by a set of first businesses and a set of fines imposed on the set of first businesses based on the set of first infractions. The trained information handling system then performs a risk assessment of a second business that includes predicting a set of possible infractions of the second business based on a set of characteristics of the second business. Then, the information handling system predicts a set of possible fines corresponding to the set of possible infractions based on the historical data. In turn, the information handling system generates a risk report that includes the set of possible infractions and the corresponding set of possible fines.

14 Claims, 10 Drawing Sheets

(56) References Cited

U.S. PATENT DOCUMENTS

| | | | |
|---|---|---|---|
| 2014/0142988 A1 | 5/2014 | Grosso et al. | |
| 2014/0372150 A1* | 12/2014 | Karle | G06Q 30/0631 |
| | | | 705/4 |
| 2015/0339572 A1* | 11/2015 | Achin | G06Q 10/06 |
| | | | 706/46 |
| 2016/0042371 A1* | 2/2016 | Klemm | G06Q 30/0203 |
| | | | 705/7.32 |
| 2016/0196445 A1 | 7/2016 | Allen et al. | |
| 2017/0024641 A1* | 1/2017 | Wierzynski | G06N 3/0454 |
| 2018/0018602 A1* | 1/2018 | DiMaggio | G06N 20/00 |

OTHER PUBLICATIONS

A Matter of Trust: The Cost of HIPAA Non-Compliance. Janet K. Feldkamp. Caring for the Ages. vol. 17, Issue 2, p. 6, Feb. 1, 2016.*
Assessing information security risk in healthcare organizations of different scale. Johnathan Coleman. International Congress Series 1268 (2004) 125-130.*
"HIPAA Assessment, HIPAA Risk Analysis," HIPAA Simple, Oct. 2017.
"HIPAA Risk Advisor, Sample Report," Sunera, Oct. 2017.
"The 4 Point HIPAA Compliance Checklist," Tech News, Snyxius, Jun. 2018, 5 pages.

* cited by examiner

| Assessing Business Risk Report 390 | | | | | |
|---|---|---|---|---|---|
| INFRACTION | PROBABILITY | POSSIBLE FINE | # PEOPLE AFFECTED | CHANGE IN SENTIMENT | CHANGE IN MARKET VALUATION |
| A | .98 | $125,000 | 1,000 | -25% | -3% |
| B | .72 | $1,300,000 | 10,000 | -25% | -12% |
| C | .45 | $35,000 | 500 | -15% | -7% |

SORT BY: PROBABILITY — 400

HEALTHCARE RISK ANALYTICS

BACKGROUND

Protection of Protected Health Information (PHI) and compliance with U.S. Health Insurance Portability and Accountability Act (HIPAA) regulation affects every healthcare business, payer and associated medical software company in the industry. This includes hospitals, urgent care centers, family physicians, specialty care, therapists, insurance companies and any identity responsible for management of data content.

Unfortunately, millions of patient records are exposed or accessed each year due to failure to implement and comply with regulatory standards. These occurrences, often referred to as breaches or failures, have resulted in over $70 M in fines imposed by the US Department of Health and Human Services (HHS) across thousands of healthcare related companies. The fines serve as motivation for businesses to adhere to regulations. In addition, the breaches typically impact the business brand negatively.

While HHS publishes a range of financial penalties associated with each violation category, HHS determines the exact amount of a financial penalty on a case-by-case basis based on the scope of the breach, the perceived impact, the business' characteristics, and the opinion of HHS on whether the business could have reasonably prevented the breach. This subjective and imprecise assessment by HHS contributes to large variations in financial penalties ranging from hundreds of dollars to several million dollars and, conversely, causes confusion in the marketplace regarding implementation priorities.

Thus, businesses need a mechanism to research and use historical HHS violation rulings in determining which HIPAA data security standards have the most risk of HHS violations in their environment and, in turn, should receive more ongoing attention, rigor and higher prioritization than other potential violations.

BRIEF SUMMARY

According to one embodiment of the present disclosure, an approach is provided in which an information handling system trains on a set of historical data that includes a set of first infractions caused by a set of first businesses and a set of fines imposed on the set of first businesses based on the set of first infractions. The trained information handling system then performs a risk assessment of a second business that includes predicting a set of possible infractions of the second business based on a set of characteristics of the second business. Then, the information handling system predicts a set of possible fines corresponding to the set of possible infractions based on the historical data. In turn, the information handling system generates a risk report that includes the set of possible infractions and the corresponding set of possible fines.

The foregoing is a summary and thus contains, by necessity, simplifications, generalizations, and omissions of detail; consequently, those skilled in the art will appreciate that the summary is illustrative only and is not intended to be in any way limiting. Other aspects, inventive features, and advantages of the present disclosure, as defined solely by the claims, will become apparent in the non-limiting detailed description set forth below.

BRIEF DESCRIPTION OF THE SEVERAL VIEWS OF THE DRAWINGS

The present disclosure may be better understood, and its numerous objects, features, and advantages made apparent to those skilled in the art by referencing the accompanying drawings, wherein:

FIG. 4 is an exemplary diagram depicting a risk report of an assessing business;

DETAILED DESCRIPTION

Figure 1:
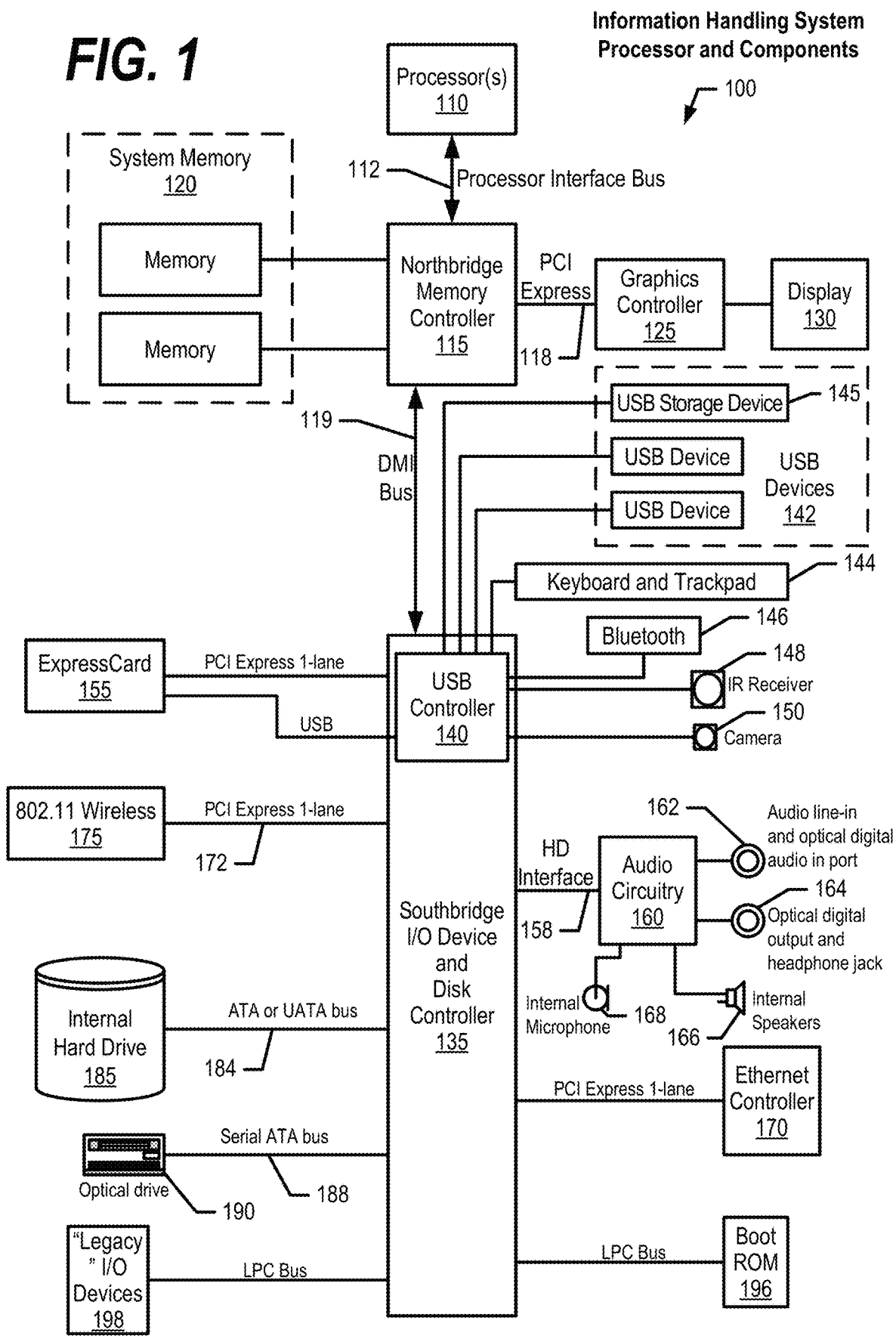
FIG. 1 is a block diagram of a representative data processing system in which the methods described herein can be implemented.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Business). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions. The following detailed description will generally follow the summary of the disclosure, as set forth above, further explaining and expanding the definitions of the various aspects and embodiments of the disclosure as necessary.

FIG. 1 illustrates information handling system 100, which is a simplified example of a computer system capable of performing the computing operations described herein. Information handling system 100 includes one or more processors 110 coupled to processor interface bus 112. Processor interface bus 112 connects processors 110 to Northbridge 115, which is also known as the Memory Controller Hub (MCH). Northbridge 115 connects to system memory 120 and provides a means for processor(s) 110 to access the system memory. Graphics controller 125 also connects to Northbridge 115. In one embodiment, Peripheral Component Interconnect (PCI) Express bus 118 connects Northbridge 115 to graphics controller 125. Graphics controller 125 connects to display device 130, such as a computer monitor.

Northbridge 115 and Southbridge 135 connect to each other using bus 119. In some embodiments, the bus is a Direct Media Interface (DMI) bus that transfers data at high speeds in each direction between Northbridge 115 and Southbridge 135. In some embodiments, a PCI bus connects the Northbridge and the Southbridge. Southbridge 135, also known as the Input/Output (I/O) Controller Hub (ICH) is a chip that generally implements capabilities that operate at slower speeds than the capabilities provided by the Northbridge. Southbridge 135 typically provides various busses used to connect various components. These busses include, for example, PCI and PCI Express busses, an ISA bus, a System Management Bus (SMBus or SMB), and/or a Low Pin Count (LPC) bus. The LPC bus often connects low-bandwidth devices, such as boot ROM 196 and "legacy" I/O devices (using a "super I/O" chip). The "legacy" I/O devices (198) can include, for example, serial and parallel ports, keyboard, mouse, and/or a floppy disk controller. Other components often included in Southbridge 135 include a Direct Memory Access (DMA) controller, a Programmable Interrupt Controller (PIC), and a storage device controller, which connects Southbridge 135 to nonvolatile storage device 185, such as a hard disk drive, using bus 184.

ExpressCard 155 is a slot that connects hot-pluggable devices to the information handling system. ExpressCard 155 supports both PCI Express and Universal Serial Bus (USB) connectivity as it connects to Southbridge 135 using both the USB and the PCI Express bus. Southbridge 135 includes USB Controller 140 that provides USB connectivity to devices that connect to the USB. These devices include webcam (camera) 150, infrared (IR) receiver 148, keyboard and trackpad 144, and Bluetooth device 146, which provides for wireless personal area networks (PANs). USB Controller 140 also provides USB connectivity to other miscellaneous USB connected devices 142, such as a mouse, removable nonvolatile storage device 145, modems, network cards, Integrated Services Digital Network (ISDN) connectors, fax, printers, USB hubs, and many other types of USB connected devices. While removable nonvolatile storage device 145 is shown as a USB-connected device, removable nonvolatile storage device 145 could be connected using a different interface, such as a Firewire interface, etcetera.

Wireless Local Area Network (LAN) device 175 connects to Southbridge 135 via the PCI or PCI Express bus 172. LAN device 175 typically implements one of the Institute of Electrical and Electronic Engineers (IEEE) 802.11 standards of over-the-air modulation techniques that all use the same protocol to wireless communicate between information handling system 100 and another computer system or device. Optical storage device 190 connects to Southbridge 135 using Serial Analog Telephone Adapter (ATA) (SATA) bus 188. Serial ATA adapters and devices communicate over a high-speed serial link. The Serial ATA bus also connects Southbridge 135 to other forms of storage devices, such as hard disk drives. Audio circuitry 160, such as a sound card, connects to Southbridge 135 via bus 158. Audio circuitry 160 also provides functionality associated with audio hardware such as audio line-in and optical digital audio in port 162, optical digital output and headphone jack 164, internal speakers 166, and internal microphone 168. Ethernet controller 170 connects to Southbridge 135 using a bus, such as the PCI or PCI Express bus. Ethernet controller 170 connects information handling system 100 to a computer network, such as a Local Area Network (LAN), the Internet, and other public and private computer networks.

While FIG. 1 shows one information handling system, an information handling system may take many forms. For example, an information handling system may take the form of a desktop, server, portable, laptop, notebook, or other form factor computer or data processing system. In addition, an information handling system may take other form factors such as a personal digital assistant (PDA), a gaming device, Automated Teller Machine (ATM), a portable telephone device, a communication device or other devices that include a processor and memory.

Figure 2:
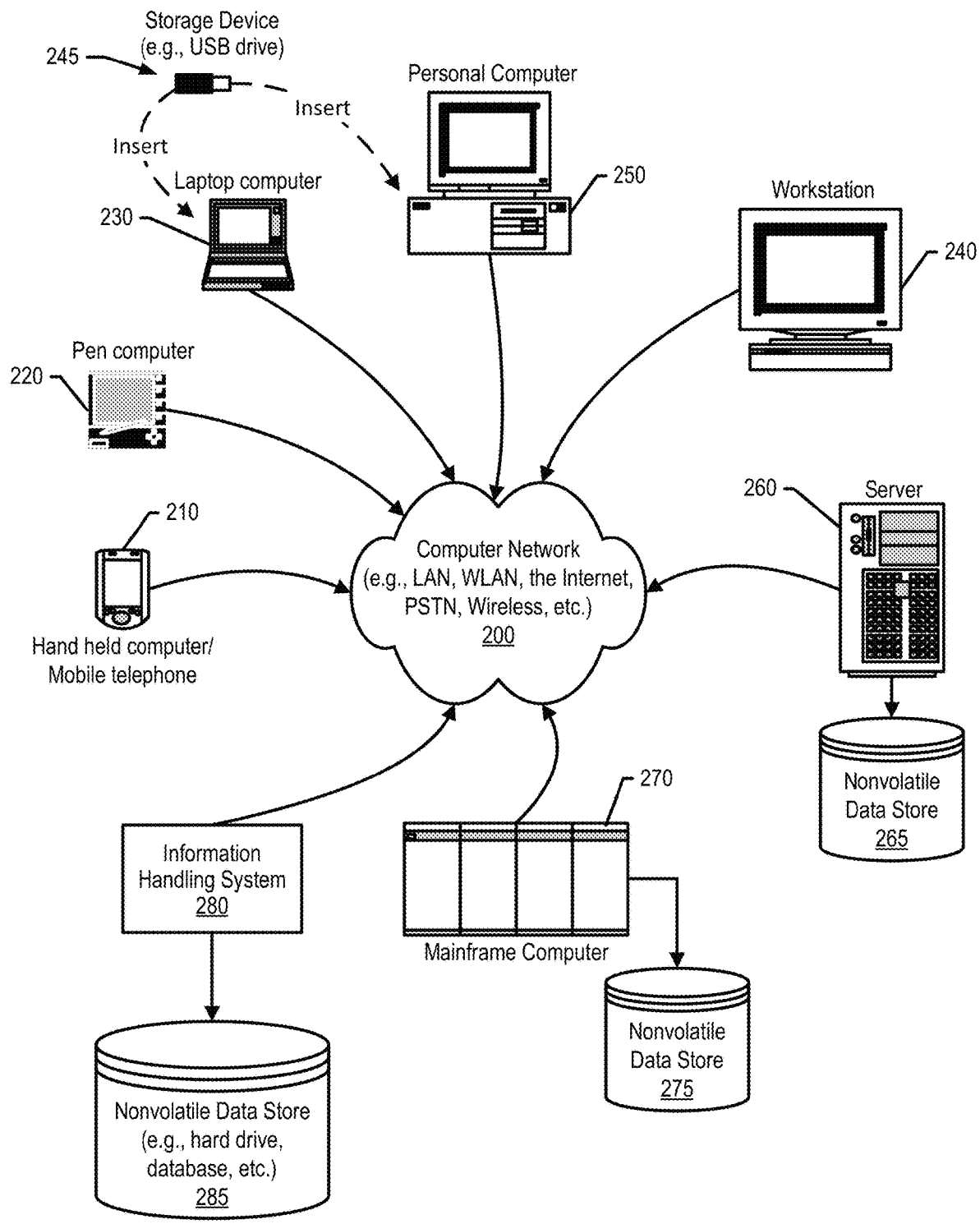
FIG. 2 provides an extension of the information handling system environment shown in FIG. 1 to illustrate that the methods described herein can be performed on a wide variety of information handling systems which operate in a networked environment.

FIG. 2 provides an extension of the information handling system environment shown in FIG. 1 to illustrate that the methods described herein can be performed on a wide variety of information handling systems that operate in a networked environment. Types of information handling systems range from small handheld devices, such as handheld computer/mobile telephone 210 to large mainframe systems, such as mainframe computer 270. Examples of handheld computer 210 include personal digital assistants (PDAs), personal entertainment devices, such as Moving Picture Experts Group Layer-3 Audio (MP3) players, portable televisions, and compact disc players. Other examples of information handling systems include pen, or tablet, computer 220, laptop, or notebook, computer 230, workstation 240, personal computer system 250, and server 260. Other types of information handling systems that are not individually shown in FIG. 2 are represented by information handling system 280. As shown, the various information handling systems can be networked together using computer network 200. Types of computer network that can be used to interconnect the various information handling systems include Local Area Networks (LANs), Wireless Local Area Networks (WLANs), the Internet, the Public Switched Telephone Network (PSTN), other wireless networks, and any other network topology that can be used to interconnect the information handling systems. Many of the information handling systems include nonvolatile data stores, such as hard drives and/or nonvolatile memory. The embodiment of the information handling system shown in FIG. 2 includes separate nonvolatile data stores (more specifically, server 260 utilizes nonvolatile data store 265, mainframe computer 270 utilizes nonvolatile data store 275, and information handling system 280 utilizes nonvolatile data store 285). The nonvolatile data store can be a component that is external to the various information handling systems or can be internal to one of the information handling systems. In addition, removable nonvolatile storage device 145 can be shared among two or more information handling systems using various techniques, such as connecting the removable nonvolatile storage device 145 to a USB port or other connector of the information handling systems. As those skilled in the art can appreciate, the approach described herein may also be implemented in a cloud computing environment, for example, a public cloud environment, a private cloud environment, a hybrid cloud environment, etc.

FIGS. 3 through 10 depict an approach that can be executed on an information handling system. The information handling system automatically evaluates and acts on healthcare business risks of a business under assessment (assessing business) by 1) acquiring historic data pertaining to fined businesses; 2) analyzing the historic data for an affinity between an assessing business and previously fined businesses; 3) generating affinity scores based on the evaluation and ranking risks to the assessing business; and 4) alerting the assessing business to a changing risk assessment. As those skilled in the art can appreciate, the approached discussed herein may be applied to other business environments that track security breaches and fines, such as credit card businesses, investment businesses, etc.

Figure 3:
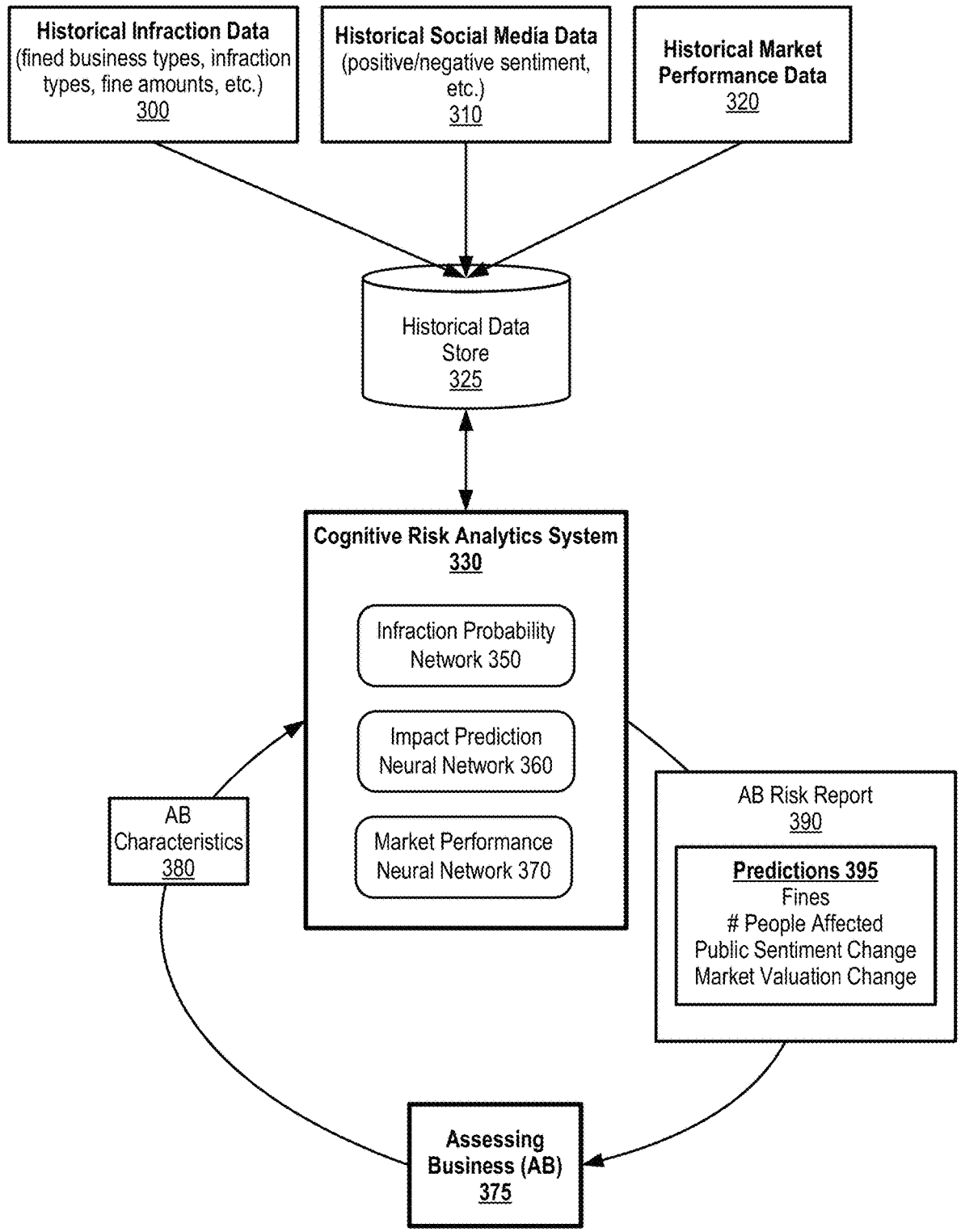
FIG. 3 is an exemplary diagram depicting a cognitive risk analytics system training on historical data and assessing a business's possible infractions and fines.

FIG. 3 is an exemplary diagram depicting a cognitive risk analytics system training on historical data using trained neural networks to assess a business's possible infractions and fines. Cognitive risk analytics system 330 provides the capability for businesses to review and evaluate, for example, historical US Department of Health and Human Services (HHS) infraction instances as a mechanism to determine their own risk and possible fines for a similar penalty.

Cognitive risk analytics system 330 trains infraction probability network 350, impact prediction neural network 360, and market performance neural network 370 on historical data that includes historical infraction data 300, historical social media data 310, and historical market performance data 320, each of which is collected and stored in historical data store 325. Historical infraction data 300 includes fined business information such as their business types, infractions committed, and amounts fined. Historical social media data 310 includes information before and after an infraction, which cognitive risk analytics system 330 utilizes to determine how social media sentiment changes when a particular infraction occurs. Historical market performance data includes market data (e.g., stock price) before and after an infraction occurs, which cognitive risk analytics system 330 utilizes to determine how a particular infraction affects market performance (see FIG. 5 and corresponding text for further details).

Cognitive risk analytics system 330 uses the historical data to train infraction probability network 350, impact prediction network 360, and market performance neural network 370 (see FIGS. 6 through 9 and corresponding text for further details). Once trained, assessing business 375 (business under assessment) provides assessing business characteristics 380 to cognitive risk analytics system 330. Assessing business characteristics may include a type of company, a number of employees, a number of clients/patients, the State of operation (e.g., Texas), and the percent of sensitive records stored electronically.

Figure 7:
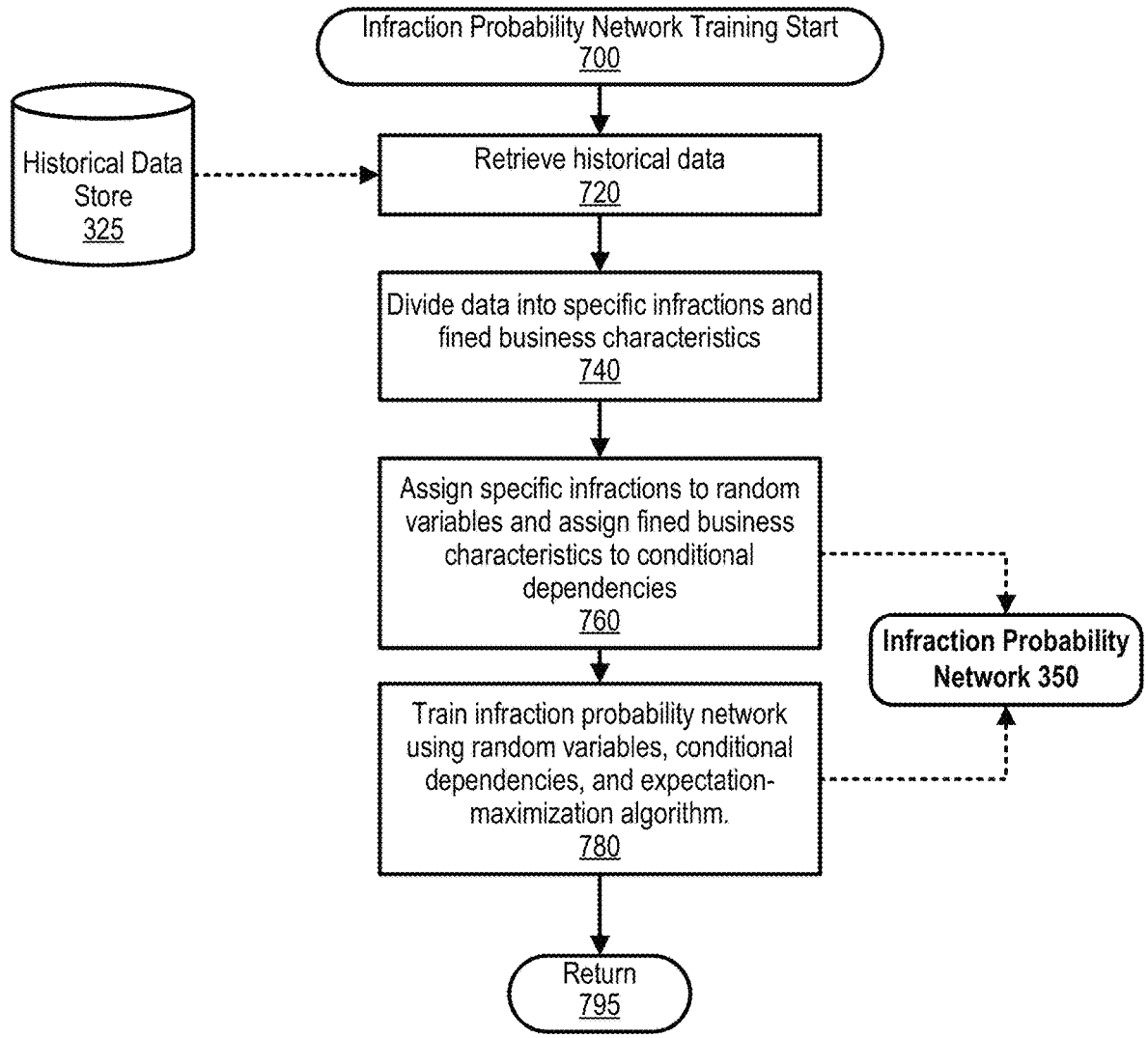
FIG. 7 is an exemplary flowchart showing steps taken to train an infraction probability network.

Cognitive risk analytics system 330 uses infraction probability network 350 to determine a relative likelihood that assessing business 375 will receive one or more infractions (see FIG. 7 and corresponding text for further details). Cognitive risk analytics system 330 then uses impact prediction neural network 360 to predict most likely impacts such as possible fines, number of individuals affected, and changes in social media sentiment. Cognitive risk analytics system 330 uses market performance neural network 370 to predict changes in assessing business 375's market performance if the possible infractions occur.

In turn, cognitive risk analytics system 330 generates assessing business risk report 390 that includes predictions 395 of possible infractions, presented in descending order of predicted risk level, along with detailed impact predictions that include possible fines, the number of individuals affected, the expected increase in negative social media attention, and the predicted resulting change in market performance (see FIG. 4 and corresponding text for further details). In turn, assessing business 375 utilizes assessing business risk report 390 to prioritize changes in how sensitive data is managed. As those skilled in the art can appreciate, more, less, or different predictions may be supplied other than what is shown in FIG. 3 and described herein.

FIG. 4 is an exemplary diagram depicting a risk report of an assessing business. Assessing business risk report 390 includes a list of possible infractions (column 410), their probability of occurring (column 420), a possible fine if the infraction occurs (column 430), the number of people affected (e.g., personal data exposed) if the infraction occurs (column 440), the change in social media sentiment (column 450), and the possible change in market valuation (column 460). A user may change how the data is sorted by selecting a different column in selection box 400.

Figure 5:
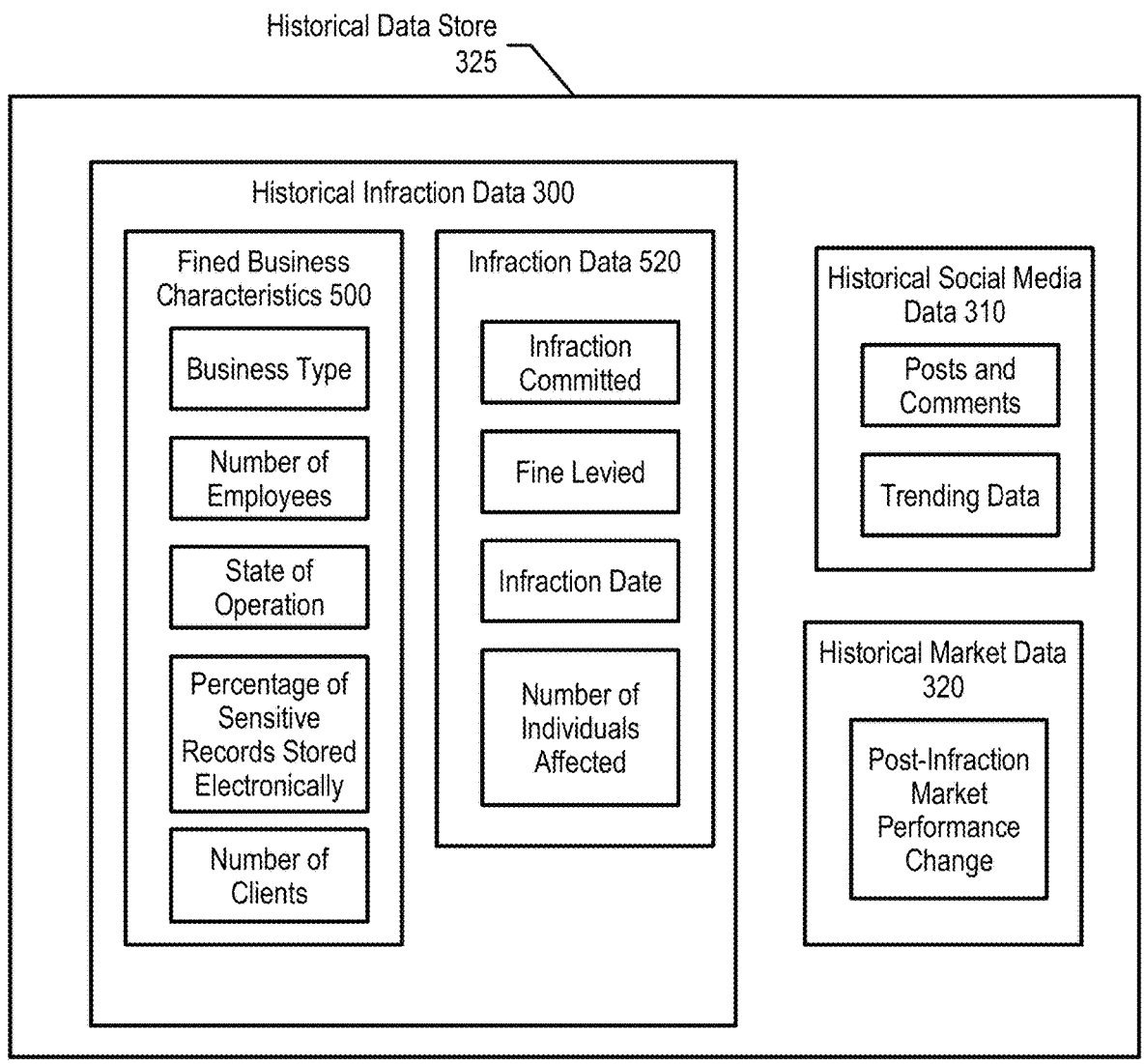
FIG. 5 is an exemplary diagram depicting collected historical data utilize by a cognitive risk analytics system to evaluate possible company violations.

FIG. 5 is an exemplary diagram depicting collected historical data utilize by cognitive risk analytics system 330 to evaluate possible company violations. As those skilled in the art can appreciate, the historical data may include more, less, and/or different information that what is shown in FIG. 5.

Historical infraction data 300 includes, for example, fined business characteristics 500 and infraction data 520. Fined business characteristics 500 includes a business type, a number of company employees, a U.S. state of operation, a percent of sensitive records stored electronically, and a number of clients or patients. Infraction data 520 includes, for example, infractions committed, fines levied, infraction dates, and number of clients or patients impacted.

Historical social media data 310 includes, for example, social media content (posts, tweets, comments, etc.) and trending sentiment data. Historical market data 320 includes, for example, market performance before and after infraction, such as stock prices before and after the infraction.

Figure 6:
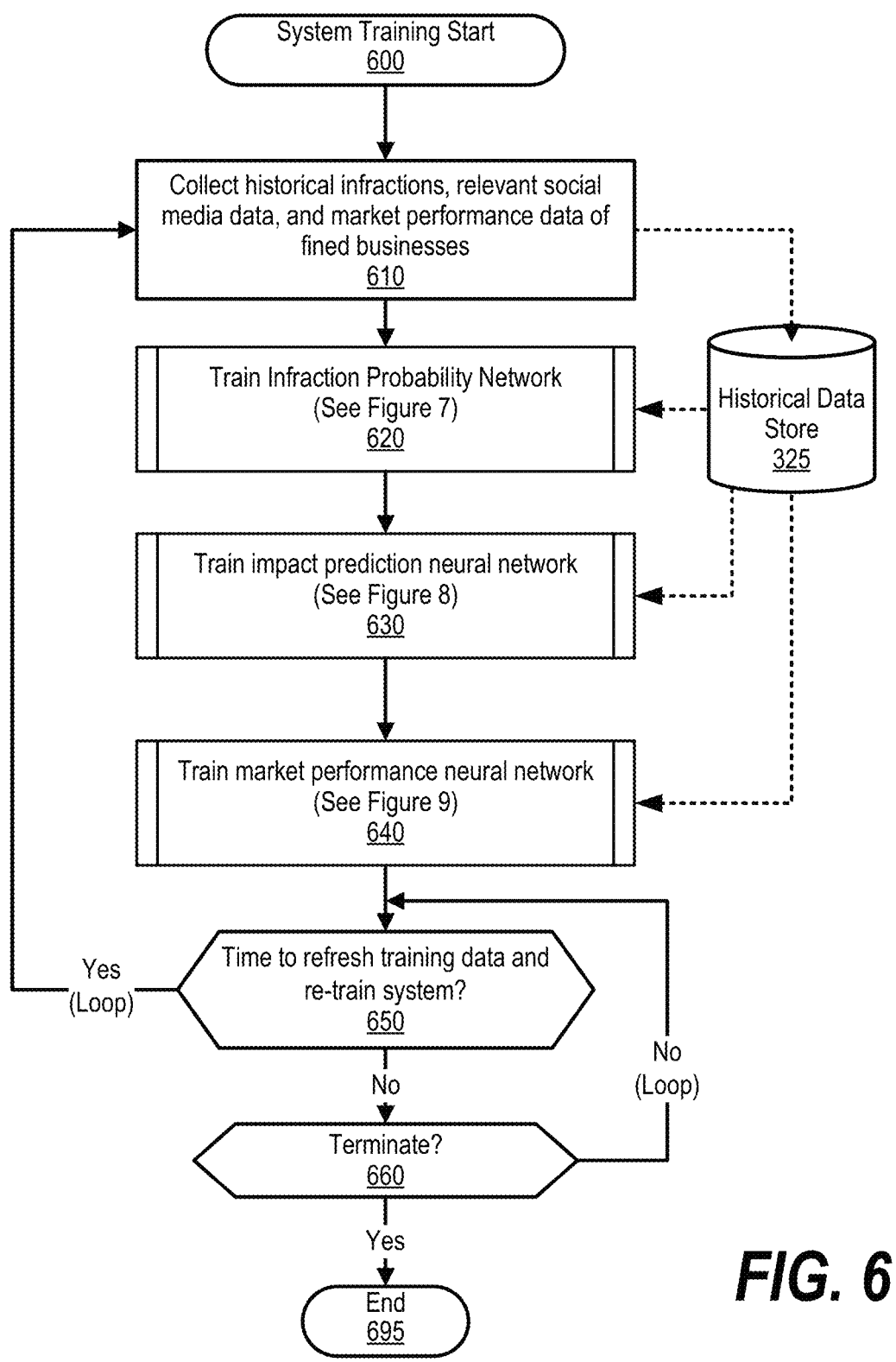
FIG. 6 is an exemplary flowchart depicting steps taken to train a cognitive risk analytics system.

FIG. 6 is an exemplary flowchart depicting steps taken to train a cognitive risk analytics system. Cognitive risk analytics system 330 first trains the cognitive components of the system using the historical data before assessing a business's possible risks. FIGS. 6 through 9 pertain to training cognitive risk analytics system 330 and FIG. 10 pertains to utilizing the trained cognitive risk analytics system 330 to assess a business and generate a report.

FIG. 6 processing commences at 600 whereupon, at step 610, the process collects historical infractions, relevant social media data, and market performance data of fined businesses, and stores the historical data in historical data store 325. Relevant social media data may be collected from major social media websites for each fined business by analyzing tweets, posts, and comments for relevance to the infraction based on keywords and hashtags. Trending data may be collected for online mentions of the fined business.

At predefined process 620, the process trains a Bayesian network that cognitive risk analytics system 330 subsequently utilizes to determine a relative likelihood that an assessing business will receive an infraction (see FIG. 7 and corresponding text for processing details).

At predefined process 630, the process trains impact prediction neural network 360 as shown in FIG. 3, which cognitive risk analytics system 330 subsequently utilizes to determine possible impact data of an infraction, such as a possible fine, the number of individuals affected, and the percent increase in negative social media attention (see FIG. 8 and corresponding text for processing details).

At predefined process 640, the process trains market performance neural network 370 as shown in FIG. 3, which cognitive risk analytics system 330 subsequently utilizes to determine possible post-infraction market performance changes, such as a change in the assessing business's stock price (see FIG. 9 and corresponding text for processing details).

The process determines as to whether it is time to refresh the training data and re-train the system (decision 650). To make this determination, in one embodiment, the process periodically queries online or proprietary databases for new infractions. If a certain amount of new infractions exist, the process retrains itself to incorporate the new knowledge into its prediction systems. To avoid training unnecessarily frequently, a threshold may be specified which must be reached before retraining will occur. This threshold could be the number of new infractions, a pre-defined period of time, or a cumulative level of impact of the new infractions. Once this threshold is reached, the system collects the new information and begins to retrain each component.

If it is time to refresh training data and re-train the system, then decision 650 branches to the 'yes' branch which loops back to collect more historical information and retrain the system. On the other hand, if it is not time to retrain the system, then decision 650 branches to the 'no' branch exiting the loop.

The process determines as to whether to terminate (decision 660). If the process should not terminate, then decision 660 branches to the 'no' branch which loops back to check if it is time to retrain the system. This looping continues until the process should terminate, at which point decision 660 branches to the 'no' branch exiting the loop. FIG. 6 processing thereafter ends at 695.

FIG. 7 is an exemplary flowchart showing steps taken to train a Bayesian network that cognitive risk analytics system 330 utilizes to determine a relative likelihood that an assessing business will receive an infraction. As discussed below, the process trains a Bayesian network using an expectation-maximization algorithm. The process takes the fined business's characteristics to be conditional dependencies for specific infractions, which are treated as random variables. In other words, the process assumes that a given fined business has committed an infraction, and will predict the most likely infraction based on the input characteristics. The expectation-maximization algorithm infers the conditional probabilities between the various characteristics and infractions from which to parameterize the network based on the historical data.

FIG. 7 processing commences at 700 whereupon, at step 720, the process retrieves historical infraction data from historical data store 325. At step 740, the process divides data into specific infractions and fined business characteristics. At step 760, the process assigns specific infractions to random variables and assigns fined business characteristics to conditional dependencies in infraction probability network 350. At step 780, the process trains infraction probability network 350 (e.g., a Bayesian network) using random variables, conditional dependencies, and expectation-maximization algorithm. FIG. 7 processing thereafter returns to the calling routine (see FIG. 6) at 795.

Figure 8:
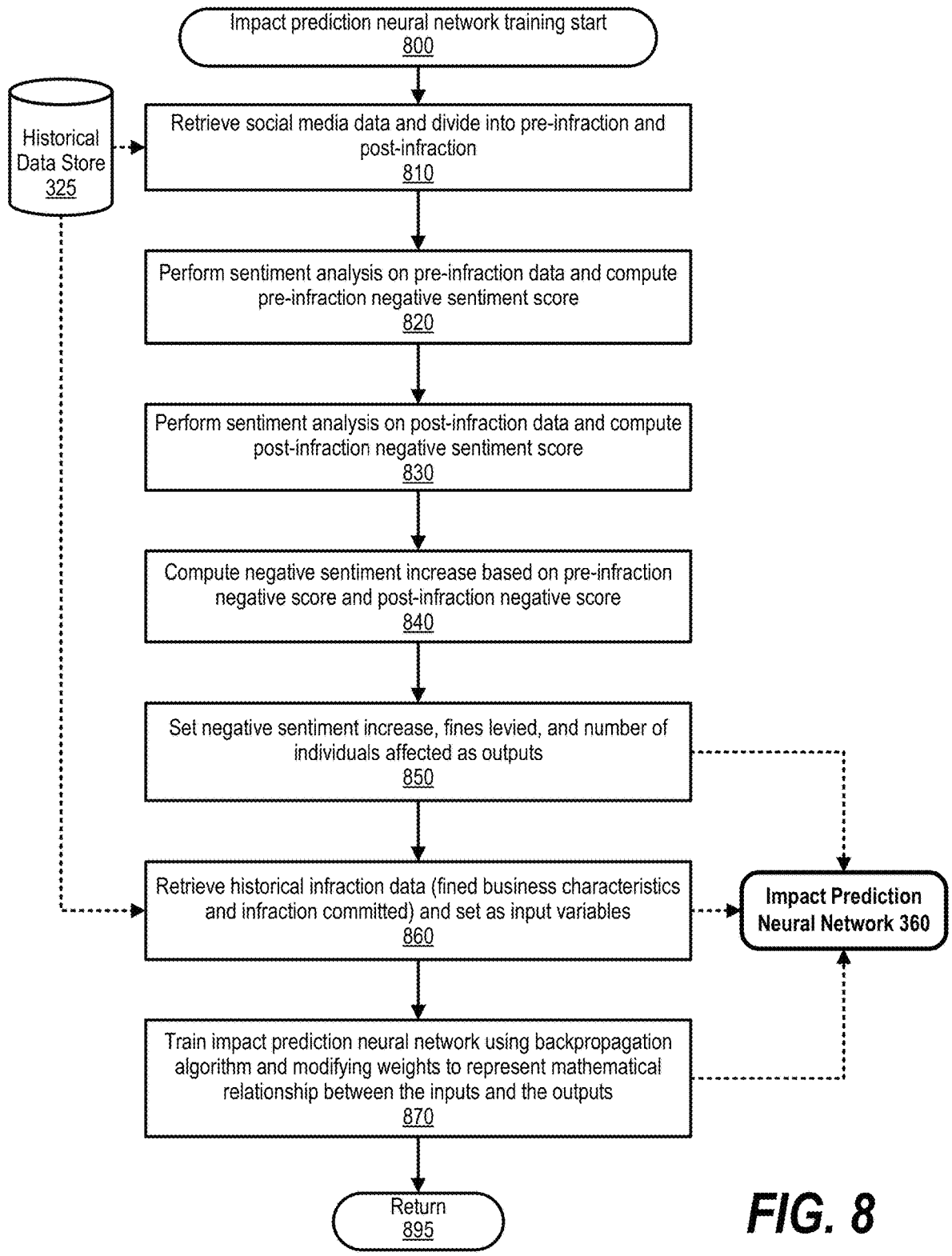
FIG. 8 is an exemplary flowchart showing steps taken to train an impact prediction neural network.

FIG. 8 is an exemplary flowchart showing steps taken to train an impact prediction neural network that is subsequently applied to the characteristics of a client company along with an infraction of concern to predict the most likely impact (see FIG. 10 and corresponding text for further details). To train the impact prediction neural network, as discussed below, the historical infraction data, including fined business characteristics and the infraction committed, are taken to be the input variables, and the fine levied, number of individuals affected, and the percent increase in negative social media attention are taken to be outputs.

Using a back propagation algorithm, the neural network's weights are modified to represent the mathematical relationship between the inputs and outputs that are present in the historical data.

FIG. 8 processing commences at 800 whereupon, at step 810, the process retrieves historical social media data 310 from historical data store 325 and divides the historical social media data into pre-infraction data and post-infraction data. As discussed below, by separating the posts pertaining to each fined business into those that came before the infraction and those that were posted after news of it broke, the increase in negative attention in response to the infraction can be measured. This percent increase is then used as an output field in the impact prediction neural network.

At step 820, the process performs sentiment analysis on the pre-infraction data and computes a pre-infraction negative sentiment score and, at step 830, the process performs sentiment analysis on the post-infraction data and computes a post-infraction negative sentiment score. At step 840, the process computes a negative sentiment increase based on the pre-infraction negative score and the post-infraction negative score.

At step 850, the process sets the negative sentiment increase, fines levied, and number of individuals affected and as outputs to impact prediction neural network 360. At step 860, the process retrieves historical infraction data of fined businesses and sets the historical infraction data as input variables to impact prediction neural network 360.

At step 870, the process trains impact prediction neural network 360 using the backpropagation algorithm and modifying weights to represent mathematical relationship between the inputs and the outputs until the impact prediction neural network produces the set outputs based on the set inputs. FIG. 8 processing thereafter returns to the calling routine (see FIG. 6) at 895.

Figure 9:
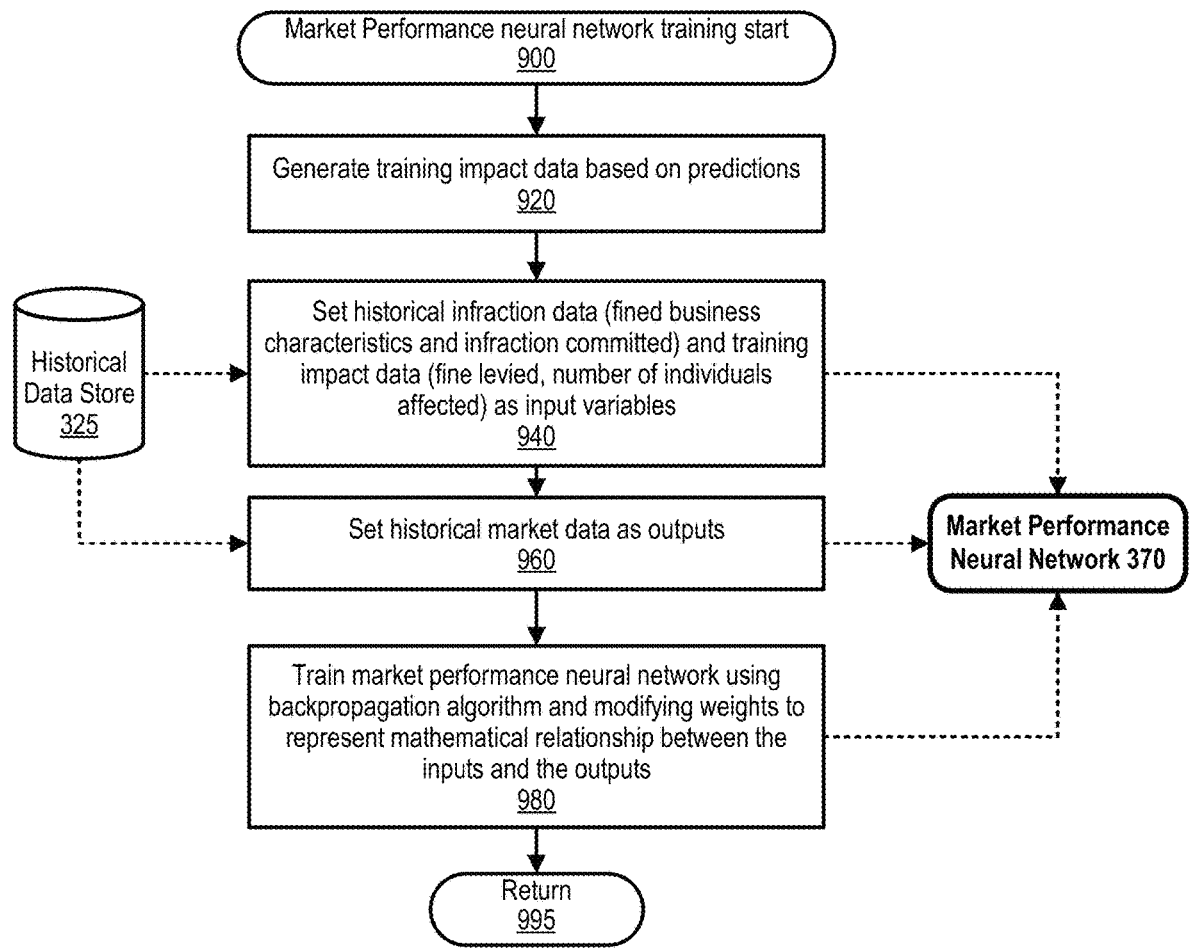
FIG. 9 is an exemplary flowchart showing steps taken to train a market performance neural network.

FIG. 9 is an exemplary flowchart showing steps taken to train a market performance neural network, which cognitive risk analytics system 330 subsequently utilizes to determine possible post-infraction market performance changes, such as a change in the assessing business's stock price. To train the market performance neural network, as discussed below, the historical infraction data is used along with the impact data and market data. The impact data, fined business characteristics, and infraction committed are taken to be inputs to the neural network, and the market data is taken to be the output of the neural network. The back propagation algorithm is again used to learn the weights of the neural network to produce the set outputs based on the set inputs. In one embodiment, during training, overlap occurs between the historical infraction data and the impact data. In this embodiment, when the network makes predictions, the "infraction committed" is hypothetical and the impact data is a set of predictions itself rather than observed data.

FIG. 9 processing commences at 900 whereupon, at step 920, the process generates training impact data based on predictions. The "impact data" includes the fine levied against the fined business for the infraction in question, the number of individuals impacted, and the percentage increase in negative social media attention the fined business received from their baseline social media sentiment. When training the market performance neural network, the fine levied and the number of individuals impacted is known (e.g., ground truth). The percentage change in negative social media attention is calculated from historical data from publicly-accessible social media sources. When using the market performance neural network to make a prediction, all three of the fields that compose "Impact Data" are the predicted values from the impact prediction neural network. The impact prediction neural network may be trained to predict these based on company characteristics and the infraction in question since they are known/calculable for the historical infraction.

At step 940, the process sets historical infraction data (fined business characteristics and infraction committed) and training impact data (fine levied, number of individuals affected) as input variables to market performance neural network 370, and at step 960, the process sets historical market data as outputs of market performance neural network 370. At step 980, the process trains market performance neural network 370 using backpropagation algorithm and modifying weights to represent mathematical relationship between the inputs and the outputs. FIG. 9 processing thereafter returns to the calling routine (see FIG. 6) at 995.

Figure 10:
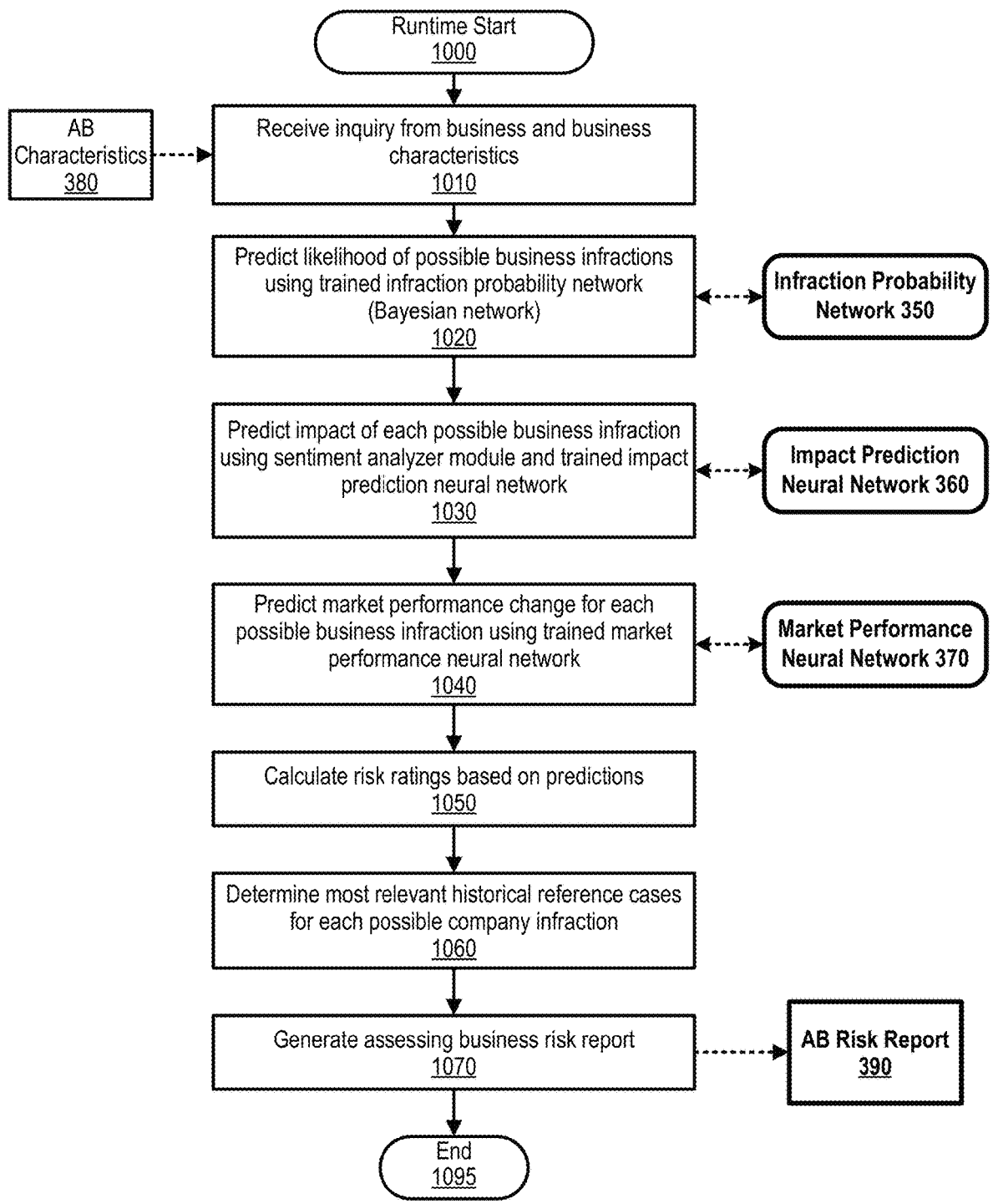
FIG. 10 is an exemplary flowchart showing steps taken to analyze an assessing business's information and generate a risk report based on historical data.

FIG. 10 is an exemplary flowchart showing steps taken to analyze an assessing business's information and generate a risk report based on historical information as discussed herein. FIG. 10 processing commences at 1000 whereupon, at step 1010, the process receives an inquiry and assessing business characteristics 380 from the assessing business. At step 1020, the process uses trained infraction probability module 350 (Bayesian network) to predict a likelihood (e.g., probability) of possible infractions of the assessing business.

At step 1030, the process uses trained impact prediction neural network 360 to predict the impact of each possible infraction. At step 1040, the process uses trained market performance neural network 370 to predict market performance change for each possible infraction. To provide the assessing business with concrete reference cases of the infractions for which they are most at risk, the process determines the historical cases of each infraction with the highest relevance to the assessing business. The process takes the most relevant historical infractions to be those committed by fined businesses with similar attribute values to the assessing business. The process selects cases involving fined businesses of the same type and operating in the same state for each infraction, ordering them based on similarity to the assessing business in the number of employees and percentage of sensitive records stored electronically. Should no cases exist for fined businesses operating in the same state, the process then considers cases involving fined businesses operating in other states.

At step 1050, the process calculates risk ratings of the possible infractions based on the predictions. The risk rating metric is proportional to the expected market performance change and relative likelihood of the infraction occurring. At step 1060, the process determines the most relevant historical reference cases for each possible infraction. At step 1070, the process generates assessing business risk report that ranks possible infractions in descending order of risk rating and are presented along with the predicted impact and market performance change for each, as well as the relative likelihood of occurrence (see FIG. 4 and corresponding text for further details). The general penalty ranges for each infraction may be provided in addition to cognitive risk analytics system 330's specific prediction. In addition, the process may locate and provide information about specific historical infractions committed by similar fined businesses. FIG. 10 processing thereafter ends at 1095.

While particular embodiments of the present disclosure have been shown and described, it will be obvious to those skilled in the art that, based upon the teachings herein, that changes and modifications may be made without departing from this disclosure and its broader aspects. Therefore, the appended claims are to encompass within their scope all such changes and modifications as are within the true spirit and scope of this disclosure. Furthermore, it is to be understood that the disclosure is solely defined by the appended claims. It will be understood by those with skill in the art that if a specific number of an introduced claim element is intended, such intent will be explicitly recited in the claim, and in the absence of such recitation no such limitation is present. For non-limiting example, as an aid to understanding, the following appended claims contain usage of the introductory phrases "at least one" and "one or more" to introduce claim elements. However, the use of such phrases should not be construed to imply that the introduction of a claim element by the indefinite articles "a" or "an" limits any particular claim containing such introduced claim element to disclosures containing only one such element, even when the same claim includes the introductory phrases "one or more" or "at least one" and indefinite articles such as "a" or "an"; the same holds true for the use in the claims of definite articles.

The invention claimed is:

1. A method implemented by an information handling system that includes a memory and a processor, the method comprising:

training, by the processor, a market performance neural network using a set of historical data that comprises a set of first infractions caused by a set of first businesses and a corresponding set of fines imposed on the set of first businesses, wherein the training further comprises:

automatically determining a set of negative sentiment increases of the set of first businesses based on the set of first infractions caused by the set of first businesses;

automatically generating a set of training impact data comprising the set of negative sentiment increase percentages, the set of fines imposed on the set of first businesses, and a number of individuals impacted by the set of first infractions;

automatically setting the set of training impact data as input variables to the market performance neural network;

automatically setting a set of historical market data as outputs to the market performance neural network, wherein the set of historical market data comprises a set of market performance changes of the first set of businesses in response to causing the set of first infractions; and automatically performing a back propagation algorithm on the market performance neural network and modifying one or more weightings in the market performance neural network to represent a mathematical relationship between the set of training impact data and the set of historical market data;

receiving a set of business characteristics from a second business, wherein the set of business characteristics comprises a company type of the second business, a number of employees of the second business, and an number of clients of the second business;

automatically generating a set of possible infractions of the second business based on the set of business characteristics;

automatically generating a set of market performance change predictions in response to inputting the set of possible infractions into the trained market performance neural network; and automatically transmitting an alert to the second business that comprises the set of possible infractions and the set of market performance change predictions.

2. The method of claim 1 further comprising:
extracting historical social media data from the set of historical data;
dividing the historical social media data into pre-infraction data and post infraction data based on a set of infraction dates corresponding to the set of first infractions;
computing a pre-infraction sentiment score based on performing a first sentiment analysis on the pre-infraction data;
computing a post-infraction sentiment score based on performing a second sentiment analysis on the post-infraction data; and
computing a negative sentiment increase based on the pre-infraction sentiment score and the post-infraction sentiment score.

3. The method of claim 1 further comprising:
in response to determining that an amount of a set of second infractions exceeds a threshold, re-training the information handling system based on the set of second infractions and a set of different fines corresponding to the set of second infractions.

4. The method of claim 1 wherein the alert comprises data, for each of the set of possible infractions, selected from the group consisting of the set of possible fines, a number of individuals affected, a change in sentiment value, and a change in market valuation.

5. The method of claim 1 wherein the set of first businesses and the second business are healthcare businesses, and wherein the set of first infractions are Health Insurance Portability and Accountability Act (HIPAA) infractions.

6. An information handling system comprising:
one or more processors;
a memory coupled to at least one of the processors;
a set of computer program instructions stored in the memory and executed by at least one of the processors in order to perform actions of:
training, by at least one of the one or more processors, a market performance neural network using a set of historical data that comprises a set of first infractions caused by a set of first businesses and a corresponding set of fines imposed on the set of first businesses, wherein the training further comprises:
automatically determining a set of negative sentiment increases of the set of first businesses based on the set of first infractions caused by the set of first businesses;
automatically generating a set of training impact data comprising the set of negative sentiment increase percentages, the set of fines imposed on the set of first businesses, and a number of individuals impacted by the set of first infractions;
automatically setting the set of training impact data as input variables to the market performance neural network;
automatically setting a set of historical market data as outputs to the market performance neural network, wherein the set of historical market data comprises a set of market performance changes of the first set of businesses in response to causing the set of first infractions; and
automatically performing a back propagation algorithm on the market performance neural network and modifying one or more weightings in the market performance neural network to represent a mathematical relationship between the set of training impact data and the set of historical market data;
receiving a set of business characteristics from a second business, wherein the set of business characteristics comprises a company type of the second business, a number of employees of the second business, and an number of clients of the second business;
automatically generating a set of possible infractions of the second business based on the set of business characteristics;
automatically generating a set of market performance change predictions in response to inputting the set of possible infractions into the trained market performance neural network; and
automatically transmitting an alert to the second business that comprises the set of possible infractions and the set of market performance change predictions.

7. The information handling system of claim 6 wherein the processors perform additional actions comprising:
extracting historical social media data from the set of historical data;
dividing the historical social media data into pre-infraction data and post infraction data based on a set of infraction dates corresponding to the set of first infractions;
computing a pre-infraction sentiment score based on performing a first sentiment analysis on the pre-infraction data;
computing a post-infraction sentiment score based on performing a second sentiment analysis on the post-infraction data; and
computing a negative sentiment increase based on the pre-infraction sentiment score and the post-infraction sentiment score.

8. The information handling system of claim 6 wherein the processors perform additional actions comprising:
in response to determining that an amount of a set of second infractions exceeds a threshold, re-training the information handling system based on the set of second infractions and a set of different fines corresponding to the set of second infractions.

9. The information handling system of claim 6 wherein the alert comprises data, for each of the set of possible infractions, selected from the group consisting of the set of possible fines, a number of individuals affected, a change in sentiment value, and a change in market valuation.

10. The information handling system of claim 6 wherein the set of first businesses and the second business are healthcare businesses, and wherein the set of first infractions are Health Insurance Portability and Accountability Act (HIPAA) infractions.

11. A computer program product stored in a computer readable storage medium, comprising computer program code that, when executed by an information handling system, causes the information handling system to perform actions comprising:
training, by a processor, a market performance neural network using a set of historical data that comprises a set of first infractions caused by a set of first businesses and a corresponding set of fines imposed on the set of first businesses, wherein the training further comprises:
automatically determining a set of negative sentiment increases of the set of first businesses based on the set of first infractions caused by the set of first businesses;

automatically generating a set of training impact data comprising the set of negative sentiment increase percentages, the set of fines imposed on the set of first businesses, and a number of individuals impacted by the set of first infractions;

automatically setting the set of training impact data as input variables to the market performance neural network;

automatically setting a set of historical market data as outputs to the market performance neural network, wherein the set of historical market data comprises a set of market performance changes of the first set of businesses in response to causing the set of first infractions; and automatically performing a back propagation algorithm on the market performance neural network and modifying one or more weightings in the market performance neural network to represent a mathematical relationship between the set of training impact data and the set of historical market data;

receiving a set of business characteristics from a second business, wherein the set of business characteristics comprises a company type of the second business, a number of employees of the second business, and an number of clients of the second business;

automatically generating a set of possible infractions of the second business based on the set of business characteristics;

automatically generating a set of market performance change predictions in response to inputting the set of possible infractions into the trained market performance neural network; and automatically transmitting an alert to the second business that comprises the set of possible infractions and the set of market performance change predictions.

12. The computer program product of claim 11 wherein the information handling system performs additional actions comprising:

extracting historical social media data from the set of historical data;

dividing the historical social media data into pre-infraction data and post infraction data based on a set of infraction dates corresponding to the set of first infractions;

computing a pre-infraction sentiment score based on performing a first sentiment analysis on the pre-infraction data;

computing a post-infraction sentiment score based on performing a second sentiment analysis on the post-infraction data; and computing a negative sentiment increase based on the pre-infraction sentiment score and the post-infraction sentiment score.

13. The computer program product of claim 11 wherein the information handling system performs additional actions comprising:

in response to determining that an amount of a set of second infractions exceeds a threshold, re-training the information handling system based on the set of second infractions and a set of different fines corresponding to the set of second infractions.

14. The computer program product of claim 11 wherein:

the alert comprises data, for each of the set of possible infractions, selected from the group consisting of the set of possible fines, a number of individuals affected, a change in sentiment value, and a change in market valuation; and the set of first businesses and the second business are healthcare businesses, and wherein the set of first infractions are Health Insurance Portability and Accountability Act (HIPAA) infractions.

* * * * *